United States Patent [19]
O'Lenick, Jr.

[11] Patent Number: 5,226,923
[45] Date of Patent: Jul. 13, 1993

[54] SILICONE FATTY ESTERS AS CONDITIONING AGENTS

[75] Inventor: Anthony J. O'Lenick, Jr., Lilburn, Ga.

[73] Assignee: Siltech Corporation, Toronto, Canada

[21] Appl. No.: 836,369

[22] Filed: Feb. 18, 1992

Related U.S. Application Data

[63] Continuation-in-part of Ser. No. 539,558, Jun. 18, 1990, Pat. No. 5,136,063.

[51] Int. Cl.$^5$ ............................................ D06M 15/647
[52] U.S. Cl. ................................. 8/115.6; 8/115.7; 8/116.1; 8/127.51; 8/129; 8/115.64; 252/8.6; 252/8.9; 252/8.57
[58] Field of Search ............ 8/115.6, 115.7, 116.1, 8/127.5, 127.51, 128.3, 128.1, 129, 115.54, 115.55, 115.56, 115.64; 252/8.9, 8.6, 8.57

[56] References Cited

U.S. PATENT DOCUMENTS

| | | | |
|---|---|---|---|
| 3,318,659 | 5/1967 | Bullock et al. | 8/115.6 |
| 3,617,187 | 11/1971 | Chitani | 8/115.6 |
| 4,380,451 | 4/1983 | Steinberger et al. | 252/8.9 |
| 4,814,409 | 3/1989 | Blevins, II et al. | 528/25 |
| 4,830,845 | 5/1989 | Ogawa et al. | 8/115.6 |
| 4,921,622 | 5/1990 | Kato et al. | 252/8.9 |
| 4,933,097 | 6/1990 | Keegan | 252/8.9 |
| 4,937,277 | 6/1990 | O'Lenick, Jr. | 524/318 |
| 5,171,476 | 12/1992 | Bloodworth et al. | 252/8.9 |

*Primary Examiner*—Prince Willis, Jr.
*Assistant Examiner*—Alan D. Diamond

[57] ABSTRACT

The invention relates to a series of novel silicone fatty esters. This class of compounds, provide outstanding softening and lubrication when applied to hair, skin, textiles and other fibers. The compounds of the present invention are prepared by reacting a the hydroxyl group in a silicone polymer with a fatty carboxylic acid, ester or anhydride.

17 Claims, No Drawings

SILICONE FATTY ESTERS AS CONDITIONING AGENTS

RELATED APPLICATIONS

This application is a continuation in part of co-pending U.S. patent application Ser. No. 07/539,558 filed Jun. 18, 1990 now U.S. Pat. No. 5,136,063.

BACKGROUND OF THE INVENTION

1. Field of the Invention

The present invention relates to a series of novel silicone fatty esters which provide outstanding lubrication, and softening when applied to a variety of fiber substrates. The esterification by which the compounds are prepared involves the reaction of a hydroxyl containing silicone polymer, and a fatty acid, ester or anhydride.

2. Arts and Practices

Silicone compounds have been known to be active at the surface of cellulosic and synthetic fibers as well as paper. They are good nondurable lubricants and are very stable to oxidation, however, their high cost and lack of efficiency at low concentrations as well as low durability have made their acceptance in commercial products quite low.

In addition to their high cost, silicone compounds have little or no solubility in mineral oils, fatty triglycerides and other classical fatty quatarnary compounds used for softening. This has resulted in the inability to prepare stable blends for use as a textile fiber treatment.

In many applications, there is a desire for a more fatty soluble softener. The desired molecule should have the desirable softening and antistatic properties of silicone, yet have compatibility with traditional fatty materials and oils. Even though a textile softener which has both the desirable softening and antistatic properties of silicone as well as compatibility with fatty compounds has been a long felt need, it isn't until the compounds of the present invention that such a system has been attained.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

THE INVENTION

Object of the Invention

It is the object of the present invention to provide novel silicone based fatty ester compounds which are substantive to the surface of a fiber and other textile materials including cellulosic material and have increased solubility in fatty materials including mineral oil, fatty triglycerides and traditional fatty quaternary ammonium compounds. The compounds of the present invention render the lubricity, and hydrophobicity generally seen in silicone compounds, but because they are esterified with fatty groups have greater solubility in hydrocarbon oils as well as fatty materials than the traditional silicone compounds which are insoluble in those materials.

It is another objective of the current invention to provide silicone fatty esters which can be used in personal care, textile, and industrial formulations to render softness and lubrication to the substrates being treated. The superior antistatic properties are an important benefit, since this is a major aspect of consumer perception of softness in consumer and industrial laundry applications. Application of the compounds of the invention can be from solvent, aqueous dispersion or solution, or applied neat in these processes.

SUMMARY OF THE INVENTION

The present invention relates to the use of novel silicone fatty ester compounds. The compounds by virtue of the fatty ester group are soluble in fatty and hydrocarbon products, but have many of the functional softening and lubrication properties of silicone. This property makes these materials excellent additives for highly effective surface modifying finishes for fiber and textiles. The compounds of the present invention are substantive to cellulosic and synthetic fibers as well as metal surfaces and plastic polymers.

The compounds of this invention are silicone fatty esters made by the esterification of a fatty acid, ester, or anhydride and a hydroxy containing silicone compound. The compounds of the present invention conform to the following structure;

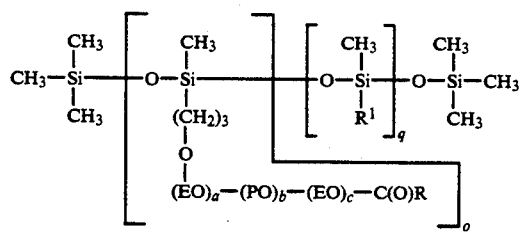

wherein;

R is alkyl having 11 to 20 carbon units;

$R^1$ is selected from lower alkyl $CH_3(CH)n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500.

PREFERRED EMBODIMENTS

In a preferred embodiment, R is $CH_3-(CH_2)_{16}-$ and is derived from stearic acid.

The compounds of the present invention can be applied from aqueous dispersion, emulsion solution or in a solvent. The effective conditioning amount of a silicone fatty ester compound generally ranges from 0.01% to 35.0% by weight.

A preferred concentration of the compounds of the present invention ranges from 1.0 to 25.0%. In a more preferred embodiment, the concentration of novel silicone ester ranges from 1.0 to 10.0%.

The compounds of the present invention have been shown to be effective when applied to a variety of fibrous materials. These include hair, cotton, polyester acrylic.

The compounds may be formulated into laundry detergents, shampoos, conditioning treatments and various formulations for application in both textile mills and fiber processing plants.

The compounds, unlike traditional quaternary compounds, have outstanding thermal stability and do not yellow the goods on which they are applied.

EXAMPLES

The compounds of the present invention are prepared by the reaction of a hydroxy silicone compound and a fatty acid. Examples of suitable reactants are as follows;

| Fatty Acids | Reactants Formula | Molecular Weight |
|---|---|---|
| Lauric | $C_{12}$ (Saturated) | 200 |
| Myristic | $C_{14}$ (Saturated) | 228 |
| Stearic | $C_{18}$ (Saturated) | 284 |
| Oleic | $C_{18}$ (monounsaturated) | 282 |
| Linoleic | $C_{18}$ (diunsaturated) | 280 |
| Hydroxystearic | $C_{18}$ (hydroxy) | 296 |

HYDROXY SILICONE COMPOUNDS

Union Carbide Chemicals and Plastics, Danbury, Conn., offers a series of hydroxy silicone compounds suitable for use as raw materials in the preparation of the esters of the present invention. These materials are marketed under the SILWET trade name. Dow Corning, Mazer and many other manufacturers also offer the compounds commercially.

The preferred method of placing this type of reactive hydroxyl group into the silicone polymer is by the reaction of silanic hydrogen containing polymer with allyl alcohol alkoxylates. This technology is well known to those skilled in the art and are described in U.S. Pat. No. 4,083,856. These hydroxyl functional silicone compounds are subsequently esterified, by reaction with fatty acids, esters or anhydrides, to make the compounds of the present invention.

Additionally, hydroxy silicone compounds are available from Siltech Inc. Norcross Ga. These compounds conform to the following generic structure;

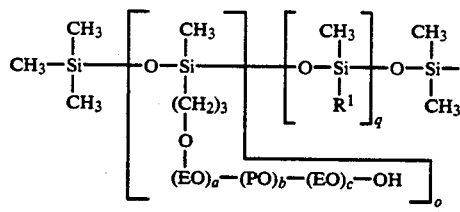

| Name | a | b | c | o | q |
|---|---|---|---|---|---|
| Siltech H 1000 | 3 | 0 | 0 | 2 | 54 |
| Siltech H 1100 | 10 | 5 | 10 | 10 | 100 |
| Siltech H 1200 | 20 | 20 | 20 | 2 | 56 |
| Siltech H 1300 | 10 | 10 | 10 | 6 | 26 |
| Siltech H 1400 | 0 | 10 | 0 | 4 | 200 |
| Siltech H 1500 | 5 | 5 | 5 | 2 | 50 |
| Siltech H 1600 | 0 | 6 | 0 | 10 | 25 |
| Siltech H 1700 | 0 | 0 | 0 | 5 | 10 |

General Reaction Conditions;

The esterification can be carried out without catalyst; however, when no catalysts are used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140° and 240° C. under an inert nitrogen blanket. The nitrogen blanket preserves the color. Preferred temperature range is between 180° and 210° C. Water is removed from the reaction which is done using a nitrogen sparge or vacuum.

The reaction can be run with either a stiochiometric amount of the fatty acid, or a slight excess of either reactant.

EXAMPLES

EXAMPLE 1

Into a suitable round bottom, three neck flask equipped with a Dean Stark trap, a thermometer and a nitrogen sparge is added 284.0 grams of stearic acid, 0.25% by weight of the total batch charged of stannous oxylate and 2.39 grams of Siltech H 1000. The reaction mass is blanketed with nitrogen, and heated to 180° and 200° C. under an inert nitrogen blanket. Once the reaction temperature reaches 120° C. water begins to boil off and is collected in the Dean Stark Trap. Within four to five hours the theoretical water is collected off and the acid value is very low. The product is a clear liquid and is used without additional purification.

EXAMPLES 2-40

Example 1 is repeated only this time substituting the specified number of grams of the fatty acid specified for the stearic acid and the specified type and number of grams of silicone compound as shown below;

| Example | Fatty Acid Type | Grams | Silicone Compound Type | Grams |
|---|---|---|---|---|
| 2 | Lauric | 200.0 | Siltech 1000 | 2,329.0 |
| 3 | Myristic | 228.0 | Siltech 1000 | 2,239.0 |
| 4 | Oleic | 282.0 | Siltech 1000 | 2,239.0 |
| 5 | Caprylic | 145.0 | Siltech 1000 | 2,239.0 |
| 6 | Stearic | 284.0 | Siltech 1100 | 2,032.0 |
| 7 | Lauric | 200.0 | Siltech 1100 | 2,032.0 |
| 8 | Myristic | 228.0 | Siltech 1100 | 2,032.0 |
| 9 | Oleic | 282.0 | Siltech 1100 | 2,032.0 |
| 10 | Caprylic | 145.0 | Siltech 1100 | 2,032.0 |
| 11 | Stearic | 284.0 | Siltech 1200 | 5,129.0 |
| 12 | Lauric | 200.0 | Siltech 1200 | 5,129.0 |
| 13 | Myristic | 228.0 | Siltech 1200 | 5,129.0 |
| 14 | Oleic | 282.0 | Siltech 1200 | 5,129.0 |
| 15 | Caprylic | 145.0 | Siltech 1200 | 5,129.0 |
| 16 | Stearic | 284.0 | Siltech 1300 | 347.6 |
| 17 | Lauric | 200.0 | Siltech 1300 | 347.6 |
| 18 | Myristic | 228.0 | Siltech 1300 | 347.6 |
| 19 | Hydroxy Stearic | 296.0 | Siltech 1300 | 347.6 |
| 20 | Caprylic | 145.0 | Siltech 1300 | 347.6 |
| 21 | Stearic | 284.0 | Siltech 1400 | 4,407.0 |
| 22 | Lauric | 200.0 | Siltech 1400 | 4,407.0 |
| 23 | Myristic | 228.0 | Siltech 1400 | 4,407.0 |
| 24 | Oleic | 282.0 | Siltech 1400 | 4,407.0 |
| 25 | Caprylic | 145.0 | Siltech 1400 | 4,407.0 |
| 26 | Stearic | 284.0 | Siltech 1500 | 2,783.0 |
| 27 | Lauric | 200.0 | Siltech 1500 | 2,783.0 |
| 28 | Myristic | 228.0 | Siltech 1500 | 2,783.0 |
| 29 | Oleic | 282.0 | Siltech 1500 | 2,783.0 |
| 30 | Caprylic | 145.0 | Siltech 1500 | 2,783.0 |
| 31 | Stearic | 284.0 | Siltech 1600 | 3,550.8 |
| 32 | Lauric | 200.0 | Siltech 1600 | 3,550.8 |
| 33 | Myristic | 228.0 | Siltech 1600 | 3,550.8 |

-continued

| Example | Fatty Acid Type | Grams | Silicone Compound Type | Grams |
|---|---|---|---|---|
| 34 | Oleic | 282.0 | Siltech 1600 | 3,550.8 |
| 35 | Caprylic | 145.0 | Siltech 1600 | 3,550.8 |
| 36 | Stearic | 284.0 | Siltech 1700 | 1,512.4 |
| 37 | Lauric | 200.0 | Siltech 1700 | 1,512.4 |
| 38 | Myristic | 228.0 | Siltech 1700 | 1,512.4 |
| 39 | Oleic | 282.0 | Siltech 1700 | 1,512.4 |
| 40 | Caprylic | 145.0 | Siltech 1700 | 1,512.4 |

APPLICATIONS EXAMPLES

Applications of the Compounds of the Invention

Compounds of this invention were compared to standard compounds commercially available using AATCC Test Method 117-1979. The color fastness heat test uses a 400° F. (205° C.) hot iron which is applied for 60 and 180 seconds. The color is rated on a 1-5 basis for yellowness, (5 being the most yellow).

| Compound | Yellowness |
|---|---|
| Alkaquat T (Imidazoline Quat) | 4 |
| Alkaquat DAET 90 (Amido Quat) | 5 |
| Example #1 | 1 |
| Example #5 | 2 |
| Example #36 | 2 |
| Example #26 | 1 |
| Example #15 | 2 |
| Siltech H 1100 | 4 |

As can be seen the compounds of the present invention are non-yellowing softeners when compared to standard softeners.

Lubrication
FRICTIONAL PROPERTIES

| PRODUCT | DESCRIPTION (70 F.) | LUBRICANT DATA[1] Coefficient of Friction FIBER/METAL | |
|---|---|---|---|
| | | 100 | 300 |
| | | (m/min.) | |
| Butyl Stearate | White Liquid | 0.17 | 0.21 |
| Tridecyl Stearate | Clear Liquid | 0.25 | 0.27 |
| Example 6 | Clear liquid | 0.10 | 0.11 |
| Example 16 | Clear Liquid | 0.07 | 0.09 |
| Example 19 | Clear liquid | 0.06 | 0.02 |
| Example 12 | Clear Liquid | 0.09 | 0.04 |
| Ditallowdimethyl benzalkonium chloride | Tan solid | 0.35 | 0.35 |
| Ditridecyl adipate | Clear Amber Liquid | 0.28 | 0.29 |
| Untreated Fiber | | 0.98 | 1.01 |

[1]Rothchild F Meter, Fiber; 150 denier polyester, Temperature: 72 F., Relative humidity; 60%

As can be easily seen the compounds of the present invention are excellent lubricants.

What is claimed:

1. A process for treating fiber which comprises contacting the fiber with an effective conditioning amount of a silicone fatty ester compound which conforms to the following structure;

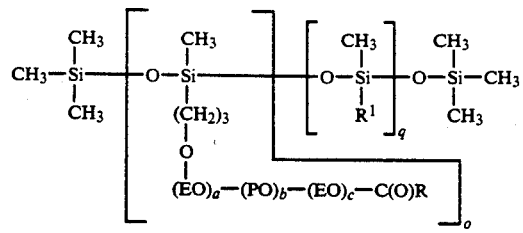

wherein;
R is alkyl having 11 to 20 carbon units;
$R^1$ is selected from lower alkyl or phenyl;
a, b and c are integers independently ranging from 0 to 20;
EO is an ethylene oxide residue $-(CH_2CH_2-O)-$;
PO is a propylene oxide residue $-(CH_2CH(CH_3)-O)-$;
o is an integer ranging from 1 to 100;
q is an integer ranging from 0 to 500.

2. A process of claim 1 wherein $R^1$ is lower alkyl.
3. A process of claim 1 wherein $R^1$ is $CH_3$.
4. A process of claim 1 wherein $R^1$ is phenyl.
5. A process of claim 1 wherein $a+b+c=0$.
6. A process of claim 1 wherein a, b and c are independently integers between 2 and 10.
7. A process of claim 1 wherein R is $CH_3-(CH_2)_{16}-$.
8. A process of claim 1 wherein R is $CH_3-(CH_2)_{14}-$.
9. A compound of claim 1 wherein R is $CH_3-(CH_2)_{12}-$.
10. A compound of claim 1 wherein R is $CH_3-(CH_2)_{10}-$.
11. A process of claim 1 wherein said effective conditioning amount of a silicone fatty ester compound ranges from 0.01 to 35.0% by weight in an aqueous dispersion, emulsion, solution, or in a solvent.
12. A process of claim 1 wherein said effective conditioning amount of a silicone fatty ester compound ranges from 1.0 to 25.0% by weight in an aqueous dispersion, emulsion, solution, or in a solvent.
13. A process of claim 1 wherein said effective conditioning amount of a silicone fatty ester compound ranges from 1.0 to 10.0% by weight in an aqueous dispersion, emulsion, solution, or in a solvent.
14. A process of claim 1 wherein said fiber is hair.
15. A process of claim 1 wherein said fiber is a textile fiber.
16. A process of claim 15 wherein said fiber is a synthetic textile fiber.
17. A process of claim 15 wherein said fiber is a natural textile fiber.

* * * * *